United States Patent
Truckai et al.

(10) Patent No.: US 12,390,243 B2
(45) Date of Patent: Aug. 19, 2025

(54) FLUID MANAGEMENT SYSTEMS AND METHODS

(71) Applicant: Meditrina, Inc., San Jose, CA (US)

(72) Inventors: Csaba Truckai, Saratoga, CA (US); Tamas J. Truckai, Saratoga, CA (US)

(73) Assignee: Meditrina, Inc., San Jose, CA (US)

( * ) Notice: Subject to any disclaimer, the term of this patent is extended or adjusted under 35 U.S.C. 154(b) by 664 days.

(21) Appl. No.: 17/303,080

(22) Filed: May 19, 2021

(65) Prior Publication Data
US 2021/0361311 A1 Nov. 25, 2021

Related U.S. Application Data

(60) Provisional application No. 63/027,554, filed on May 20, 2020.

(51) Int. Cl.
*A61B 17/32* (2006.01)
*A61B 17/00* (2006.01)

(52) U.S. Cl.
CPC ...... *A61B 17/32002* (2013.01); *A61B 2017/0023* (2013.01); *A61B 2017/0046* (2013.01); *A61B 2017/320032* (2013.01); *A61B 2217/005* (2013.01); *A61B 2562/0247* (2013.01)

(58) Field of Classification Search
CPC ...... A61B 17/32002; A61B 17/320016; A61B 17/320036; A61B 2017/0023; A61B 2017/0046; A61B 2017/320032; A61B 2017/320024; A61B 2017/320028; A61B 2217/005
See application file for complete search history.

(56) References Cited

U.S. PATENT DOCUMENTS

| | | | |
|---|---|---|---|
| 7,647,263 B2 * | 1/2010 | Daul | G06Q 40/08 705/36 R |
| 9,655,639 B2 | 5/2017 | Mark | |
| 2005/0065538 A1 | 3/2005 | Van Wyk | |
| 2011/0125055 A1 | 5/2011 | Privitera et al. | |
| 2013/0072936 A1 * | 3/2013 | To | A61B 17/1671 606/79 |
| 2013/0296847 A1 * | 11/2013 | Germain | A61B 18/1485 606/39 |
| 2014/0140815 A1 * | 5/2014 | Shener-Irmakoglu | A61B 17/32002 417/478 |
| 2015/0327880 A1 | 11/2015 | Wasicek et al. | |
| 2016/0346036 A1 * | 12/2016 | Orczy-Timko | A61B 18/1206 |
| 2017/0252099 A1 * | 9/2017 | Orczy-Timko | A61B 18/14 |
| 2017/0360466 A1 * | 12/2017 | Brown | A61B 17/32002 |
| 2018/0250029 A1 | 9/2018 | Begg | |
| 2019/0104932 A1 * | 4/2019 | Truckai | A61B 17/320016 |
| 2019/0134279 A1 | 5/2019 | Benamou et al. | |

(Continued)

FOREIGN PATENT DOCUMENTS

| | | |
|---|---|---|
| JP | 2015-083201 | 4/2015 |
| JP | 2016-537093 | 12/2016 |

(Continued)

*Primary Examiner* — Anh T Dang
(74) *Attorney, Agent, or Firm* — Levine Bagade Han LLP

(57) ABSTRACT

Single-use devices that carry at least one peristaltic pump for providing fluid flows in hysteroscopic or similar procedures. single-use handheld device with a motor-driven cutter and an integrated peristaltic pump used for resecting and removing tissue in an endoscopic procedure.

14 Claims, 8 Drawing Sheets

(56) References Cited

U.S. PATENT DOCUMENTS

2019/0223898 A1* 7/2019 Curtin ............. A61B 17/32002
2020/0289319 A1* 9/2020 Carter ................ A61F 9/00763

FOREIGN PATENT DOCUMENTS

| WO | WO 2016/028507 | 2/2016 |
| WO | WO 2019/189078 | 10/2019 |
| WO | WO 2020/097448 | 5/2020 |
| WO | WO 2021/237242 | 11/2021 |

* cited by examiner

FLUID MANAGEMENT SYSTEMS AND METHODS

RELATED APPLICATION INFORMATION

This application is a non-provisional of U.S. Provisional application 63/027,554 filed on May 20, 2020, the entirety of which is incorporated by reference.

BACKGROUND OF THE INVENTION

1. Field of the Invention

The present invention relates to single-use devices that carry at least one peristaltic pump for providing fluid flows in hysteroscopic or similar procedures that in one variation includes a single-use handheld device with a motor-driven cutter and an integrated peristaltic pump that is used for resecting and removing tissue in an endoscopic procedure.

SUMMARY OF THE INVENTION

The present disclosure includes tissue resecting devices and methods of their use. For example, a variation of a tissue resecting device can comprise a handle carrying a motor drive. The tissue resecting device can also comprise an elongated sleeve assembly coupled to the handle. The elongated sleeve can have an outer sleeve with a distal opening for receiving tissue. The elongated sleeve can also have a moveable inner sleeve adapted to resect tissue received by a window at a distal end of the inner sleeve. The tissue resecting device can also comprise a peristaltic pump and a tissue trap carried by the handle.

The motor drive can be adapted to move the inner sleeve and resect tissue. The motor drive can also be adapted to provide negative pressure in a passageway in the inner sleeve to thereby aspirate fluid and resected tissue through the passageway and into the tissue trap. The motor drive can move the inner sleeve axially, rotationally, or both. The tissue trap can be positioned proximally or distally relative to the motor drive. The peristaltic pump can have a rotational axis aligned with the rotational axis of a shaft of the motor drive. The tissue trap can be detachable from the handle. The tissue trap can include a transparent material.

The motor drive can further be adapted to operate at a plurality of selected speeds to thereby provide a corresponding plurality of selected levels of negative pressure. The motor drive can be adapted to rotate the inner sleeve at a selected speed between 100 rpm and 5,000 rpm. The motor drive can also be adapted to adapted provide a negative pressure to cause an outflow rate between 10 ml/min and 1,000 ml/min.

The tissue resecting device can further comprise a gear mechanism. The gear mechanism can provide oscillating rotation of the inner sleeve with the motor drive rotating in a single direction. The tissue resecting device can further comprise a second peristaltic pump carried by the handle. The second peristaltic pump can be adapted for providing fluid inflows from a fluid source through a channel in the sleeve assembly to a distal end thereof.

The present disclosure also includes fluid management systems. For example, a variation of such a fluid management can comprise a housing, a first peristaltic pump, a second peristaltic pump, and at least one motor. The first peristaltic pump can be carried by the housing and can be adapted to provide fluid inflow to a treatment site. The first peristaltic can engage flexible tubing that extends from a fluid source. The second peristaltic pump can be carried by the housing and can be adapted to provide fluid outflows from the treatment site. The second peristaltic pump can engage flexible tubing that extends to a tissue catch. The at least one motor can be carried by the housing and can operate the first and second peristaltic pumps.

The at least one motor can be adapted to provide inflow and outflow rates between 10 ml/min and 1,000 ml/min. The single-use fluid management system can further comprise a pressure sensor adapted to measure fluid pressure in the fluid inflow. The single-use fluid management system can further comprise a controller adapted to maintain a set pressure in a working space responsive to signals from the pressure sensor.

The descriptions provided herein are examples of the invention described herein. It is contemplated that combinations of specific embodiments, specific aspects or combinations of the specific embodiments themselves are within the scope of this disclosure.

BRIEF DESCRIPTION OF THE DRAWINGS

Additional aspects of the invention will become clear from the following description of illustrative embodiments and from the attached drawings, in which.

DETAILED DESCRIPTION OF THE INVENTION

Figure 1:
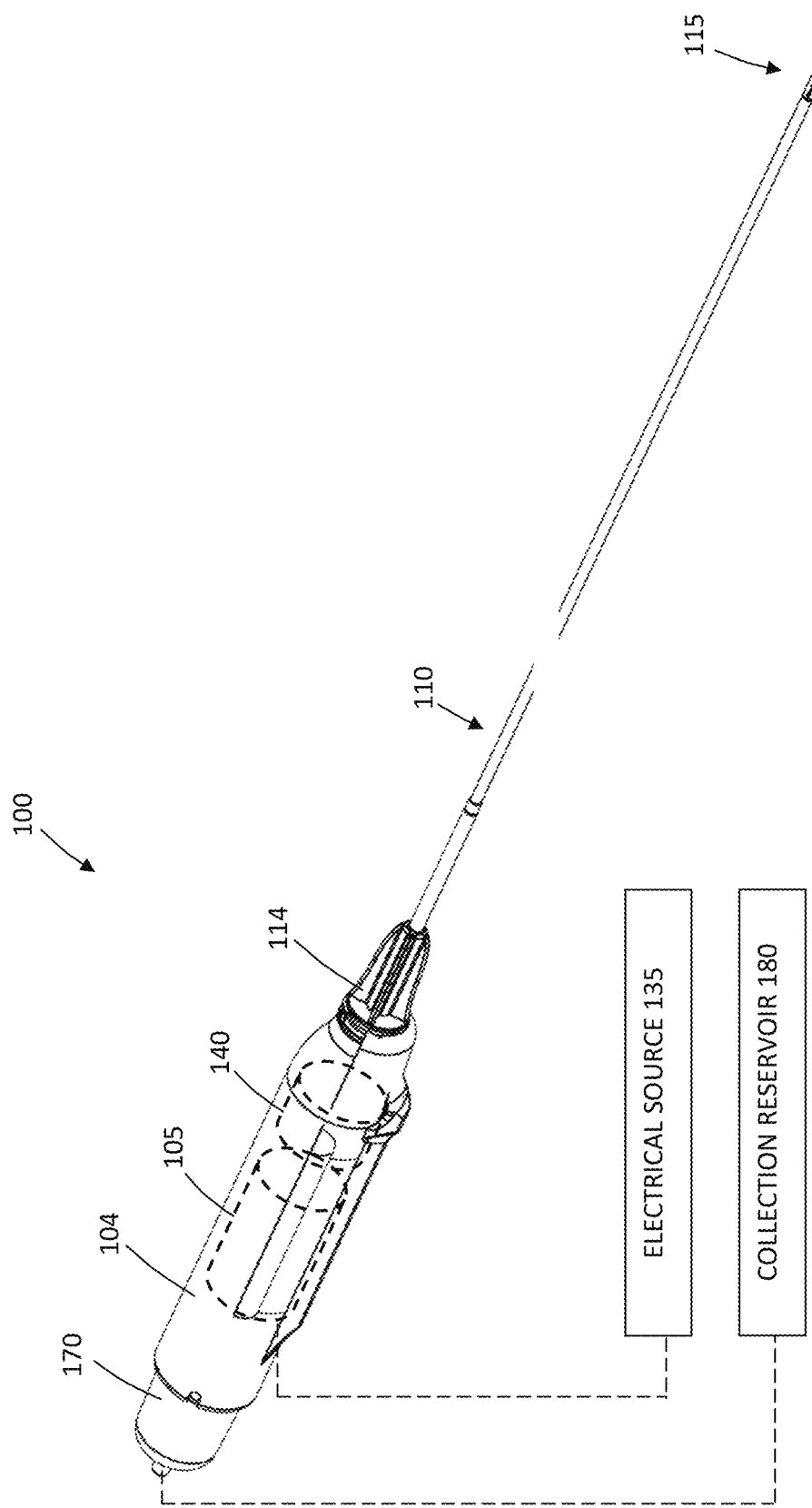
FIG. 1 is a perspective view of single-use tissue resecting device which includes a handle carrying a motor drive adapted to rotate a tubular cutter at a distal working end of an elongate shaft assembly wherein the motor drive is adapted to contemporaneously operate a peristaltic pump within the handle that is adapted to suction fluid and resected tissue from a treatment site.
Figure 2:
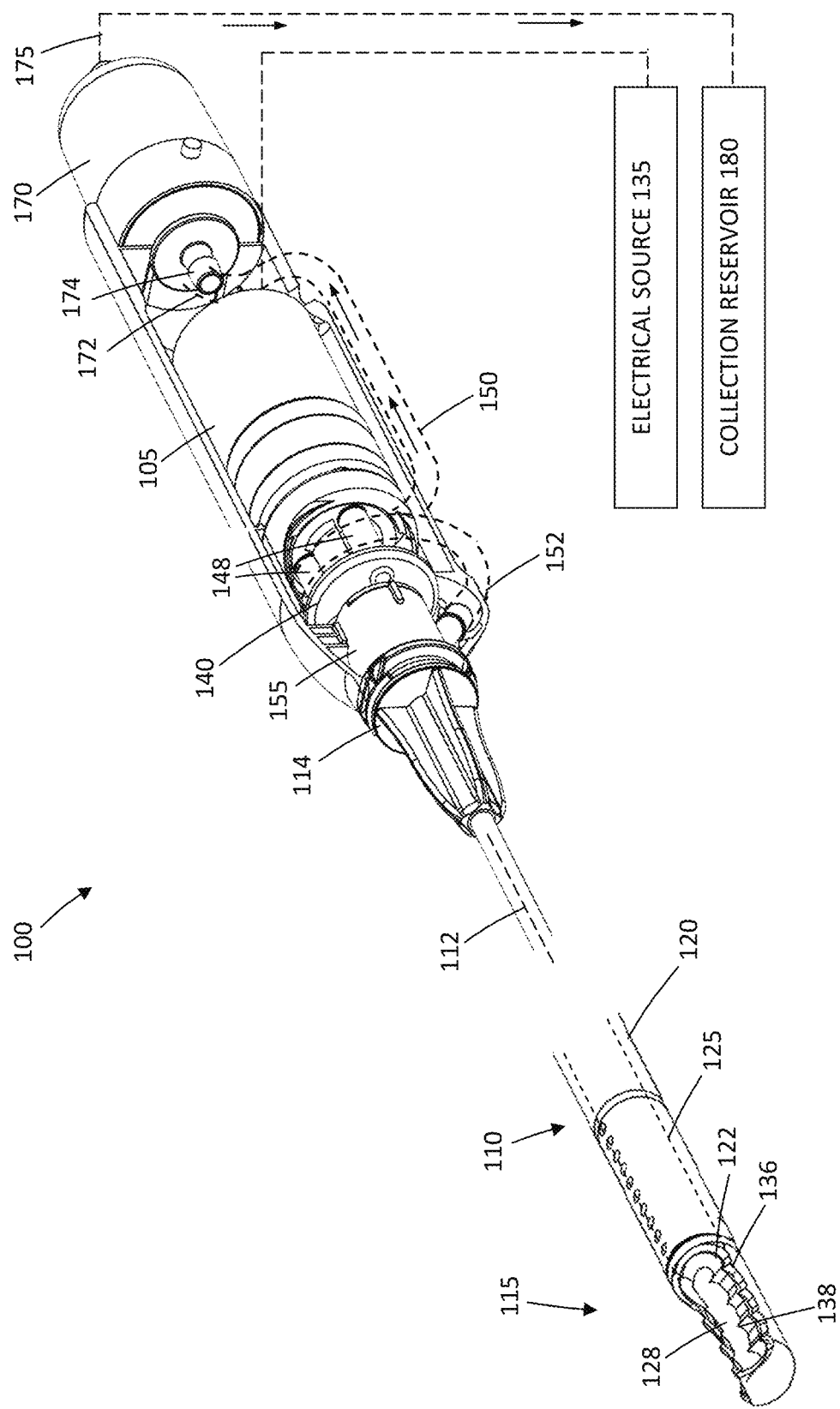
FIG. 2 is a perspective view of the device of FIGS. 1 and 2 showing the handle partly disassembled to show the peristaltic pump, the motor drive and a tissue catch together with an enlarged view of the working end of the elongate shaft assembly.
Figure 3:
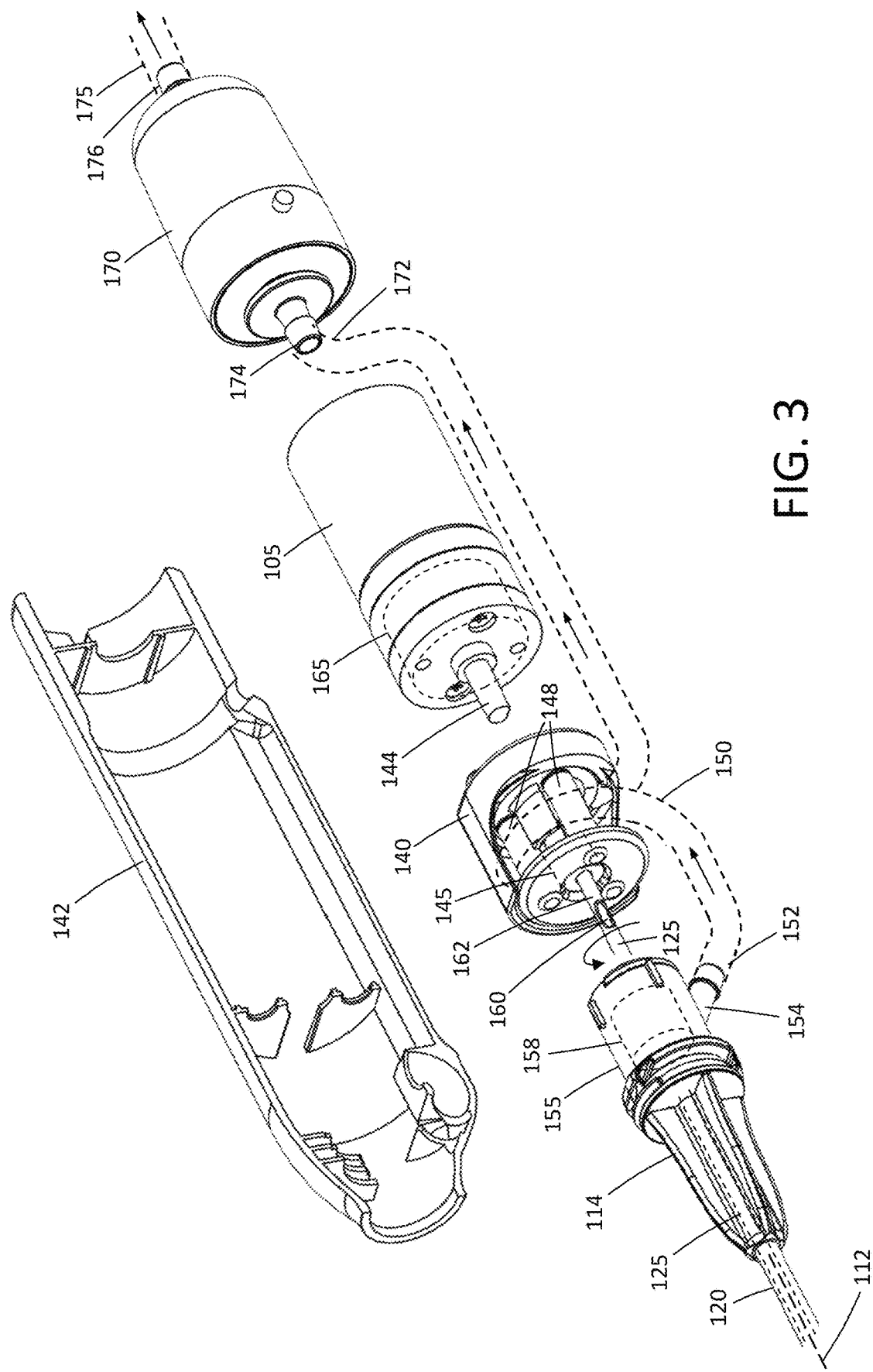
FIG. 3 is an exploded view of the components in the interior of the handle of FIG. 1, showing the peristaltic pump, the motor drive and the tissue catch.

FIGS. 1 through 3 illustrate a motor-driven resecting device 100 that is designed for single-use, typically in a hysteroscopic procedure to resect and remove a polyp, a fibroid or other abnormal uterine tissue. As is known in the art, sterilization of re-usable handles with motor drives is complex and expensive. The cost of sterilization as well as the risks of infection from improperly sterilized devices makes single-use device less expensive to a hospital or physician's office, when compared to using sterilizable devices.

Referring to FIGS. 1 and 2, the handle or handpiece 104 includes a motor drive 105 and is coupled to an elongate shaft or sleeve assembly 110 extending about longitudinal axis 112. The shaft assembly 110 extends distally from a rotatable hub 114 to the working end 115. In one variation, the elongated shaft assembly 110 comprises an outer sleeve 120 with a distal window 122 and a motor-driven, rotating inner sleeve 125 with a window 128 therein (see FIGS. 2 and 5). The motor drive 105 is coupled to an electrical source 135 and is adapted to rotate the inner sleeve 125 as further described below. (see FIGS. 2 and 3). Such a type of tubular cutter is known in the art wherein the rotating inner sleeve 125 cuts tissue that interfaces with window 122 in the outer sleeve 120 as the inner sleeve window 128 rotates or oscillates at high speed. Either or both windows 122 and 128 may be configured with cutting teeth, with FIG. 2 illustrating teeth 136 on outer window 122 and teeth 138 on inner window 128.

As can be understood from FIGS. 1 and 2, the rotating hub 114 of the shaft assembly 110 is coupled to the handle 104 so that the physician can rotate the shaft assembly 110 and working end 115 relative to the handle 104 to any rotational orientation for cutting tissue while maintaining the handle 104 in an upright or stable position. The handle 104 can include an actuator button (not shown) for actuating the motor drive 105 or a footswitch can be used.

Referring to FIGS. 1 and 2, in one variation, the tissue resecting device 100 has a shaft assembly 110 with a diameter ranging from 2 mm to 6 mm, and more often the diameter is between 3 mm and 5 mm. The shaft assembly 110 has a diameter and length for cooperating with a working channel of an endoscopic viewing system or other introducer.

As is known in the prior art, typically a fluid management system is used in a hysteroscopic resection procedures to expand a patient's uterine cavity to allow for endoscopic viewing. In one variation shown in FIGS. 1 and 2, the resecting device 100 includes a peristaltic pump 140 carried in the interior of the handle 104 which thus comprises a component of a fluid management system. More in particular, the peristaltic pump 140 is configured to provide fluid outflows from a treatment site, where the fluid inflows can be provided by a simple fluid inflow mechanism, such as gravity flow from a hanging saline bag.

FIG. 2 shows the handle 104 of FIG. 1 with a first side of the exterior shell 142 removed to show the motor drive 105 and peristaltic pump 140. In a variation, the handle 104 carries an inexpensive, DC electric motor drive 105 which allows for its disposability. As can be seen in the exploded view of FIG. 3, the motor drive 105 has a drive shaft 144 that connects a central shaft 145 of the peristaltic pump 140 which has rollers 148 aligned with the axis 112 of the drive shaft 144. The peristaltic pump 140 is of a conventional design with 3 or 4 rollers that are adapted to engage flexible tubing 150 shown in phantom view. The flexible tubing 150 has a distal end 152 that couples to a fitting 154 in a housing portion 155 of the rotatable hub 114. The flexible tubing 150 can be disposed with a space in the handle 104 or can be secured by retention clips in an inferior surface of the handle. The interior lumen of the tubing 150 communicates with a chamber 158 in the housing 155 which is open to a fluid port 160 in the proximal end 162 of the rotating inner sleeve 125 (FIG. 3). In FIG. 3, it further can be seen that the proximal end 162 of inner sleeve 125 is fixed to the central shaft 145 of the peristaltic pump 140. Thus, in the variation of FIGS. 2 and 3, the motor drive 105 is configured to rotate the inner sleeve 125 and peristaltic pump 140 at the same RPM, which can be from 100 RPM to 5,000 RPM. In one variation, the motor drive 105 provides a negative pressure to cause an outflow rate between 10 ml/min and 1,000 ml/min.

Referring again to FIGS. 2 and 3, the handle 104 further carries a tissue trap 170 of a type know in the art where fluid outflow and tissue chips are carried into the tissue trap 170 by the peristaltic pump 140 and the tissue trap has a filter that captures the resected tissue chips in a filter, where the tissue chips can be collected for biopsy purposes. In one variation, the tissue trap 170 is made of a transparent material to allow viewing of the tissue chips. In FIG. 3, the direction of fluid outflows is indicated by arrows in the tubing 150. The proximal end 172 of the tubing is connected to a fitting 174 in the tissue trap 170. Another length of tubing 175 couples to a proximal fitting 176 of the tissue trap 170 which extends to a remote collection reservoir 180 (FIGS. 1-2).

Figure 4:
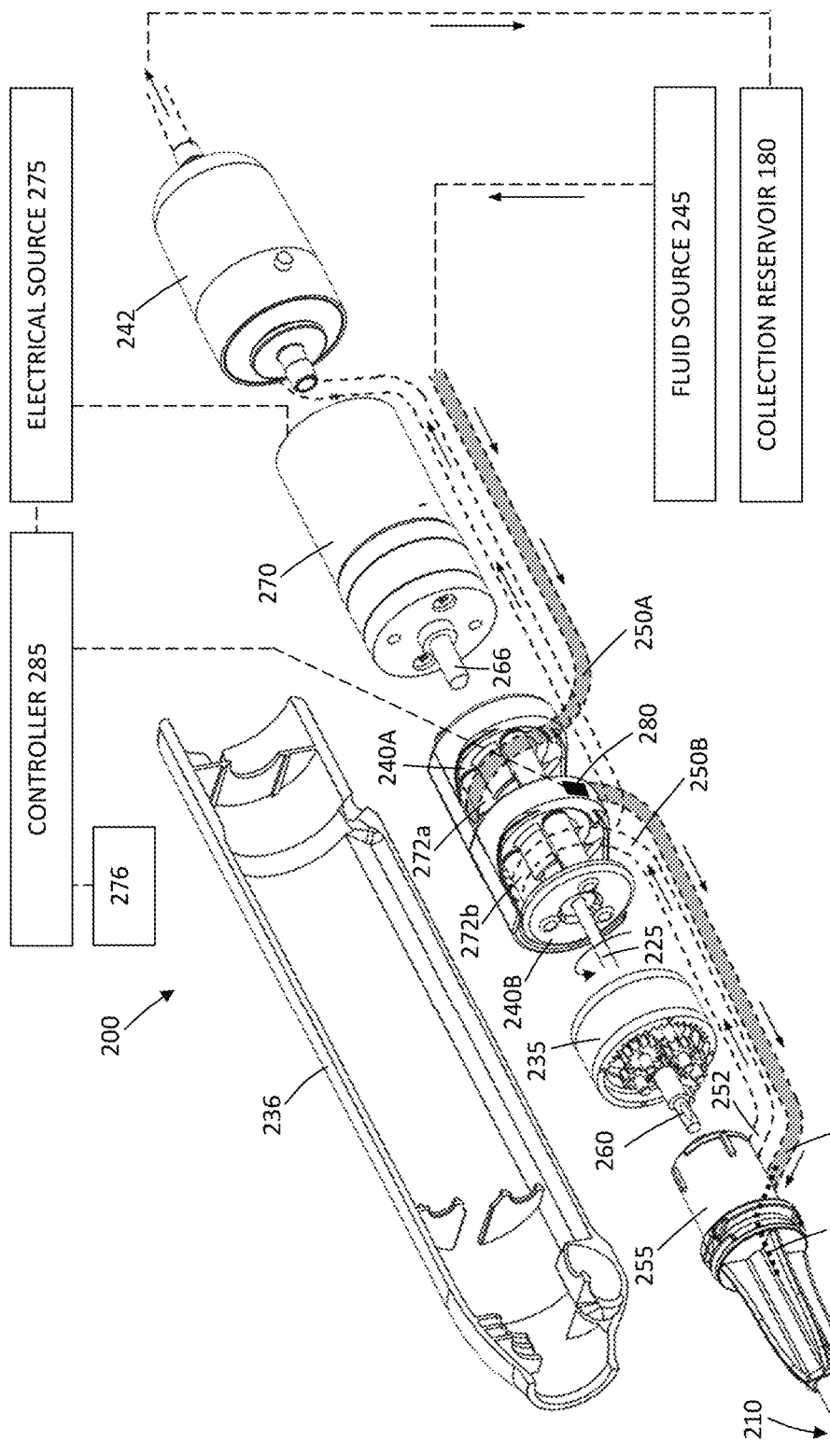
FIG. 4 is an exploded view of another variation of a device similar to that of FIGS. 1-3, wherein the components in the interior of the handle include an inflow peristaltic pump, an outflow peristaltic pump, a motor drive, a tissue catch and a gear assembly configured for converting unidirectional rotation of the motor shaft into an oscillating rotational movement of a tubular cutting member in the working end of the shaft assembly.
Figure 5:
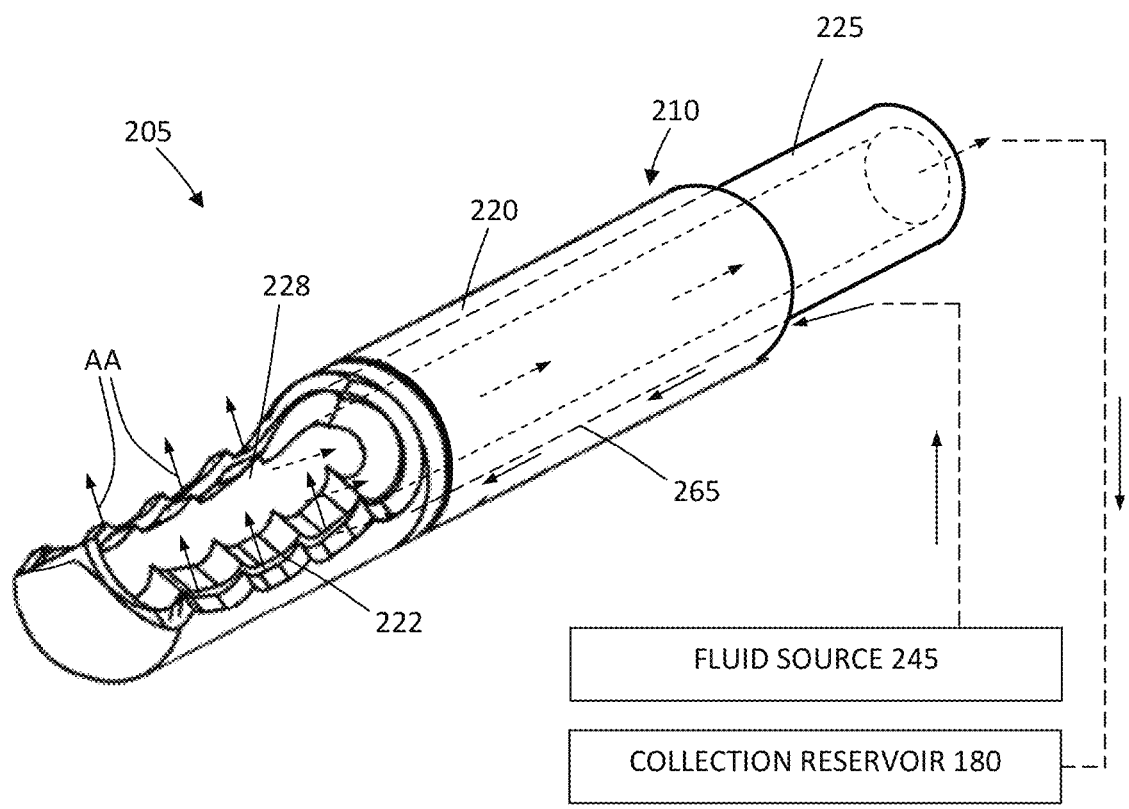
FIG. 5 is an enlarged perspective view of the working end of the device of FIG. 4, which is similar to the working end of FIG. 2, showing the fluid inflow channel communicating with the inflow peristaltic pump and further showing the tissue extraction passageway communicating with the outflow peristaltic pump.

FIG. 4 is an exploded view of another variation of a resection device 200 and FIG. 5 is an enlarged view of the working end 205 of the device 200 of FIG. 4. In this variation, the shaft assembly 210 remains the same with an outer sleeve 220 and window 222 with a motor-driven inner sleeve 225 and window 228 for resecting tissue.

The resection device 200 of FIGS. 4 and 5 differs from the previous embodiment in that a gear mechanism 235 is carried within the handle 236 to oscillate rotation of the inner sleeve 225 instead of unidirectional rotation. Further, the handle 236 carries a first peristaltic pump 240A for providing fluid inflows and a second peristaltic pump 240B for providing fluid outflows as described previously. In one aspect of the invention, the device 200 carries all the components of a fluid management system with both inflow and outflow pumps and a tissue catch 242. In the exploded view of FIG. 4, the first inflow peristaltic pump 240A is in fluid communication with a fluid source 245, such as a saline bag. The pump 240A engages flexible tubing 250A that extends to the fluid source 245. The outflow peristaltic pump 240B engages flexible tubing 250B which operates as described previously, with the distal end 252 of the outflow tubing 250B communicating with a chamber (nor shown) in housing 255 which receives fluid and tissue chips from port 260 in inner sleeve 225 (see FIG. 3).

As can be understood from FIGS. 4 and 5, the distal end 262 of inflow tubing 250 a connect to a passageway 264 in housing 255 that further communicates with in an inflow channel 265 in the shaft assembly 210 which consists of the annular space in the bore of the outer sleeve 220 and outward of the outer surface of the inner sleeve 225 (FIG. 5). Turning to FIG. 5 which shows the working end 205, it can be seen that fluid inflows are indicated by arrows AA where the fluid exits the space between the inner sleeve 225 and outer sleeve 220. The motor drive 270 can be adapted provide inflow and outflow rates between 10 ml/min and 1,000 ml/min. The motor drive 270 is operatively coupled to an electrical source 275 which may be a battery in the handle or a remote battery or power source. Actuation of the system can be provided by a switch 276 in the handle or a foot switch.

Referring to FIG. 4, both peristaltic pumps 240A and 240B can be a conventional design with 3 or 4 rollers engage the flexible tubing 250A and 250B, respectively. Both pumps 240A and 240B can be connected to motor shaft 266 of motor drive 270. As can be seen in FIG. 4, the pumps 240A and 240B can rotate in the same direction, but the flexible tubing 250A and 250B can be disposed around the roller 272a and 272b of the pumps in opposing directions (i.e., one clockwise and the other counterclockwise) to that fluid flow in opposing directions in the tubing. In other variations, the handle 232 can be provided with a single motor and gear mechanisms to drive the pumps in opposing directions, or the handle can be provided with an individual motor for each pump. While peristaltic pumps 240A and 240B are shown in the figures, it should be appreciated that other types of pumps can be used, such as piston pumps, impeller pumps, vane pumps and the like.

Referring again to FIG. 4, the exploded view of handle 236 shows the gear mechanism 235 which converts the single direction of rotation of the motor drive shaft 266 to an oscillating rotation of the inner sleeve 225 to thus provide and oscillating movement of the inner sleeve cutting window 228 at the working end 205 of the device 200 (See FIG. 5). As is well known in the field of tissue resection, tubular cutters work optimally when the inner rotating sleeve and inner cutting window 228 oscillates, for example, with several revolutions in one rotational direction followed by a similar number of rotations in the opposite direction. Such oscillation provides improved cutting performance when compared with devices that rotate a cutting member in a single direction. The gear mechanism 235 is more fully described in commonly owned U.S. patent application Ser. No. 16/678,647 titled ENDOSCOPE AND METHOD OF USE filed Nov. 8, 2019, which is incorporated herein by reference. The gear mechanism 235 can operate at any suitable rotation speed, for example 100 RPM to 5000 RPM or more.

In another aspect of the invention, the peristaltic pumps 240A and 240B of the resecting device 200 can provide different flow rates, wherein one flow rate (inflow or outflow rate) can range from 50% to 100% of the other flow rate. Such varied inflow and outflow rates can be provided for any constant pump rotational speed by varying the interior lumen diameter of the inflow tubing 250A and the outflow tubing 250B. Alternatively, a gear mechanism can be provided to rotate the pumps at different rotational speeds, for any given motor speed.

In another optional variation, a device 200 as in FIG. 4 can include a pressure sensor 280 positioned to measure pressure in the inflow line 250A distal to the pump 250A. The pressure sensor 280 can be configured to send pressure signals to a processor or controller 285 which in turn can include control algorithms for actuation of the pumps. In another variation, the device 200 can be provided with first and second motor drives (not shown) coupled to the respective pumps 240A and 240B, and the controller 285 can control operation of the pumps independently to maintain a set pressure in a treatment site based on pressure readings by the pressure sensor 280.

While FIG. 4 shows two separate peristaltic pumps 240A and 240B, it should be appreciated that a single peristaltic pump with elongated rollers may be configured with inflow and outflow tubing disposed opposing rotational directions around the roller to provide the inflows and outflows.

While FIG. 4 shows on variation of a handle design in which the pumps 240A and 240B, gear mechanism 235, motor 270 and tissue catch 242 are positioned in a particular longitudinal arrangement, these components can be positioned in any suitable manner within the handle 236.

Figure 6:
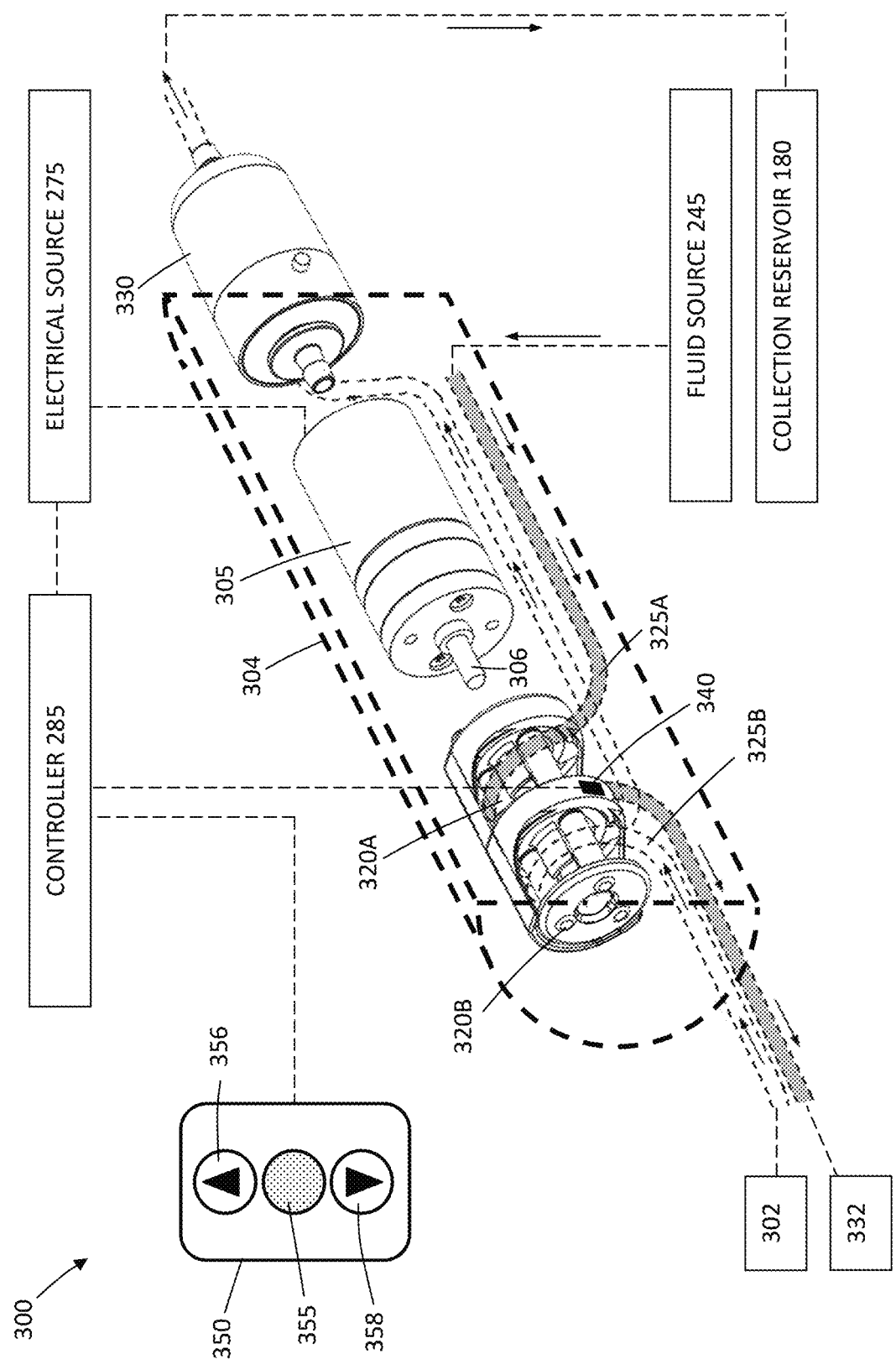
FIG. 6 is an exploded view of a single-use fluid management system wherein a housing carries an inflow peristaltic pump, an outflow peristaltic pump, a motor drive and a tissue catch.
Figure 7:
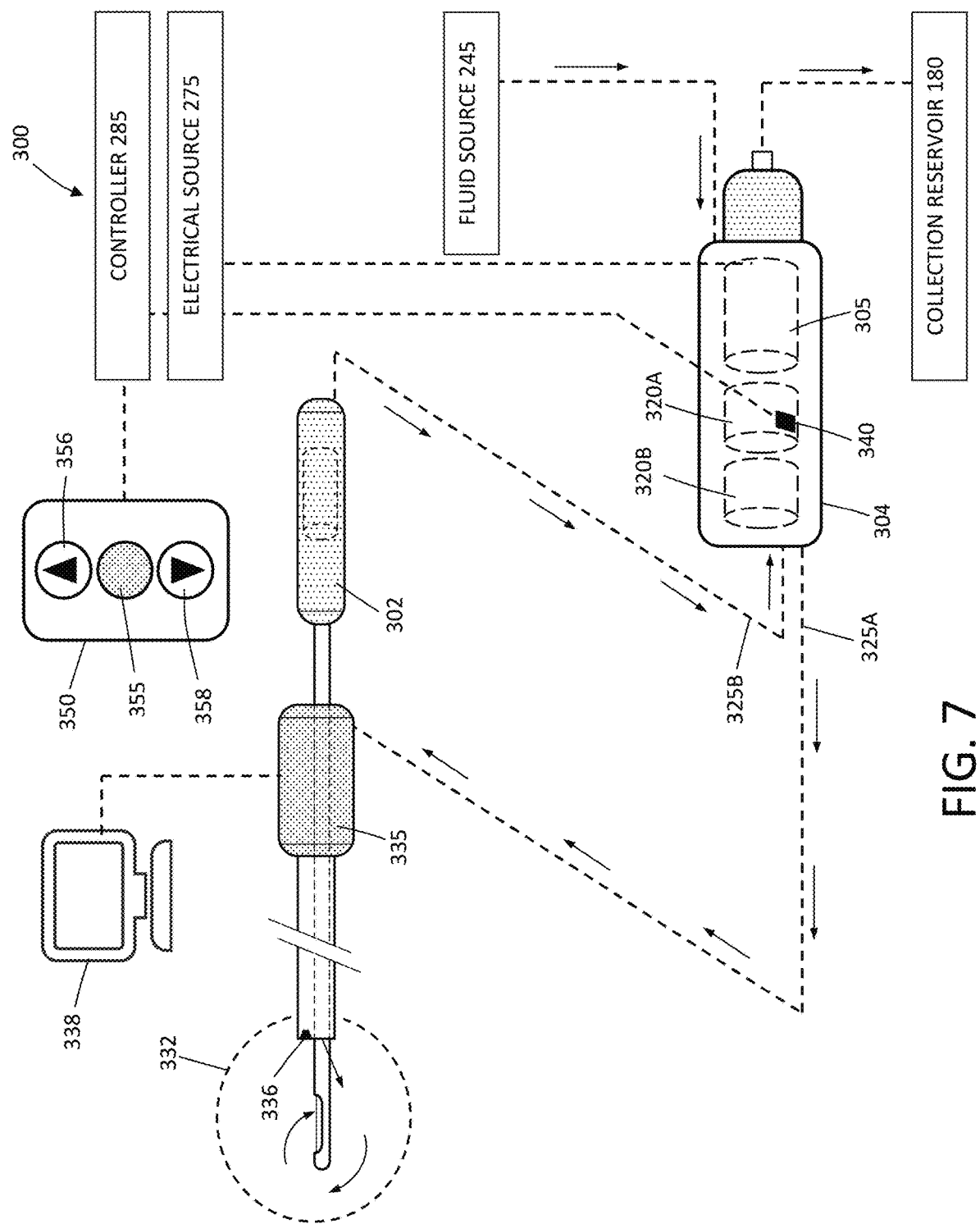
FIG. 7 is a schematic view of the single-use fluid management system of FIG. 6.
Figure 8:
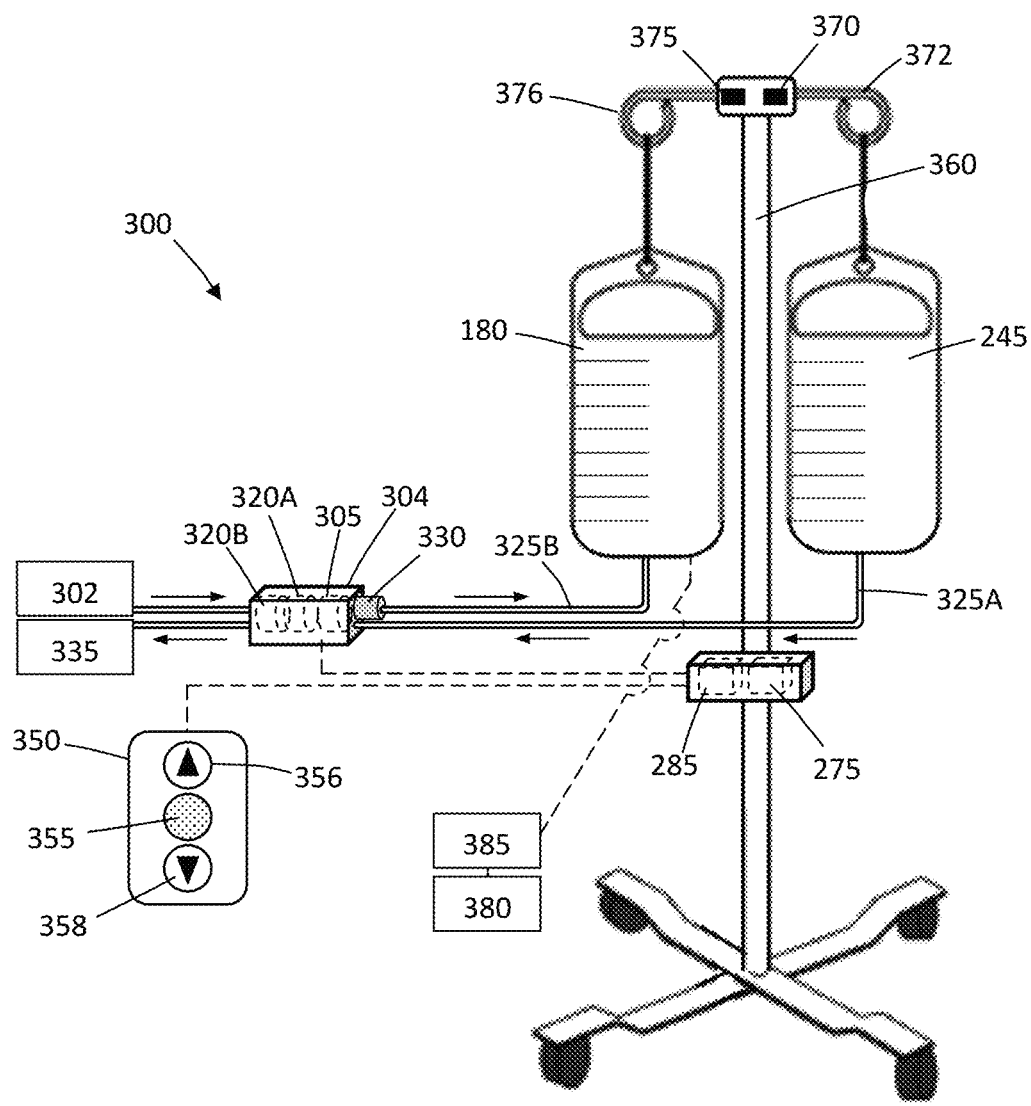
FIG. 8 is another view of the single-use fluid management system of FIGS. 6 and 7 showing the system components mounted on a roll-stand.

FIGS. 6, 7 and 8 illustrate schematically another variation of the invention which comprises a single-use fluid management system 300 that can be used for diagnostic procedures or that can be used with a separate resection device 302 in shown in FIG. 7 in a resection procedure. In a hysteroscopic diagnostic procedure, both the fluid inflow and outflow lines would be connected to an endoscope. In a resection procedure, the fluid inflow would be connected to an endoscope and the outflow line would be connected to the resection device.

In FIG. 6, it can be seen that the fluid management system 300 consists of a housing 304 that carries a motor drive 305 with motor shaft 306 that drives peristaltic pump portions 320A and 320B that are similar to the pumps in the previously described system. The peristaltic pumps 320A and 320B engage respective tubing sets 325A and 325B to provide fluid inflows and outflows. A fluid source 245 and collection reservoir 180 are provided as in the previous system. A tissue catch 330 also is the same as described previously. The fluid inflows from pump 320A are configured to flow into a working space 332, such as a uterine cavity, as shown in FIG. 7. The inflow can be directed through an inflow channel in an electronic endoscope 335 with image sensor 336 as shown in FIG. 7. The endoscope 335 is coupled to display 338. The motor drive 305 is connected to an electrical source 275 which is either a battery in the housing 304 or a remote battery or power source, which may be connected to the controller 285 further described below.

In the fluid management system 300 of FIGS. 6 and 7, a pressure sensor 340 again is positioned to measure pressure in the inflow line 325A distal to the pump 320A. The pressure sensor 340 is configured to send pressure signals to the processor or controller 285. In this variation, the controller 285 may be adapted for single use or can be re-useable and carried in suitable housing which also may carry the battery or power source 275. The controller 285 includes control algorithms for actuation of the pumps 320A and 320B for maintaining a set pressure in the working space 332, such as a uterine cavity, in response to pressure signals from the sensor 340.

In order to operate the fluid management system 300, a control pad 350 is coupled to the controller 285, which can include an ON/OFF button 355 for actuating the pumps. Further, the control pad 350 can include buttons 356 and 358 for increasing and decreasing the set pressure. Another button (not shown) can be provided for a "flush" mode wherein the fluid flow rate is increased to a higher level for flushing the working space 332. The control pad can be disposable and attached to the handle of the endoscope 335 when performing a diagnostic procedure or can be attached to the handle of a resecting device 302 in a resection procedure. In use, a saline bag comprising the fluid source 245 and the collection reservoir (e.g., a plastic bag) 180 can be hung on a stand 360 as shown in FIG. 8. The controller 285 can comprise a small housing that also can be attached to the stand 360 carrying the saline bag 245. The single-use disposable fluid management system 300 can be positioned in any suitable location for coupling to the endoscope 335 and optionally to the resecting device 302. The system thus occupies a very small footprint compared to commercially available fluid management systems.

In a variation shown in FIG. 8, the stand 360 can include a first load sensor 370 operatively connected to a first hook 372 carrying the saline bag 245 (fluid source) and a second load sensor 375 connected to a second hook 376 carrying the collection reservoir 180, wherein both load sensors send signals to the controller 285. The controller 285 then can use controller algorithms as known in the art to calculate a fluid deficit. Other variations can include using a single load sensor that weighs both the saline bag 245 and the collection reservoir 180 as is known in the art. In another variation, the system can include a drape 380 and separate pump 385 for pumping fluid collected by a drape 380 to the collection reservoir 180 which can allow for more accurate calculation of fluid deficits.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A tissue resecting device comprising:
a handle carrying a motor drive comprising a drive shaft;
an elongated sleeve assembly coupled to the handle, the elongated sleeve assembly having an outer sleeve comprising a distal opening for receiving tissue and a plurality of outer teeth, and a moveable inner sleeve adapted to resect tissue received by an inner window at a distal end of the inner sleeve, wherein the inner window comprises a plurality of inner teeth configured to resect tissue received in the distal opening;
a peristaltic pump carried by the handle, wherein the peristaltic pump comprises one or more rollers, wherein a proximal end of the inner sleeve is fixed to a central shaft of the peristaltic pump, wherein the central shaft contacts each of the one or more rollers and connects to the drive shaft such that the motor drive is configured to rotate the central shaft and the one or more rollers with respect to a longitudinal axis of the elongated sleeve assembly; and
a tissue trap carried by the handle;
wherein the motor drive is adapted to move the inner sleeve to resect tissue, and adapted to provide negative pressure in a passageway in the inner sleeve to aspirate fluid and resected tissue through the passageway and into the tissue trap.

2. The tissue resecting device of claim 1 wherein the motor drive moves the inner sleeve rotationally.

3. The tissue resecting device of claim 1 wherein the motor drive moves the inner sleeve axially.

4. The tissue resecting device of claim 1 wherein the motor drive moves the inner sleeve axially and rotationally.

5. The tissue resecting device of claim 1 wherein the tissue trap is positioned proximally relative to the motor drive.

6. The tissue resecting device of claim 1 wherein the peristaltic pump is positioned distally relative to the motor drive.

7. The tissue resecting device of claim 1 wherein the peristaltic pump has a rotational axis aligned with the rotational axis of a shaft of the motor drive.

8. The tissue resecting device of claim 1 wherein the tissue trap is detachable from the handle.

9. The tissue resecting device of claim 1 wherein the tissue trap includes a transparent material.

10. The tissue resecting device of claim 1 wherein the motor drive is adapted to operate at a plurality of selected speeds to thereby provide a corresponding plurality of selected levels of negative pressure.

11. The tissue resecting device of claim 1 wherein the motor drive is adapted to rotate the inner sleeve at a selected speed between 100 rpm and 5,000 rpm.

12. The tissue resecting device of claim 1 wherein the motor drive is adapted provide a negative pressure to cause an outflow rate between 10 ml/min and 1,000 ml/min.

13. The tissue resecting device of claim 1 further comprising a gear mechanism for oscillating rotation of the inner sleeve with the motor drive rotating in a single direction.

14. The tissue resecting device of claim 1 further comprising a second peristaltic pump carried by the handle adapted for providing fluid inflows from a fluid source through a channel in the elongated sleeve assembly to a distal end thereof.

* * * * *